US 8,388,666 B2

(12) United States Patent
Castaneda et al.

(10) Patent No.: US 8,388,666 B2
(45) Date of Patent: Mar. 5, 2013

(54) LOCKING SCREW SYSTEM WITH RELATIVELY HARD SPIKED POLYAXIAL BUSHING

(75) Inventors: Javier E. Castaneda, Miami, FL (US); Robert Graham, Miami, FL (US); Cesare Cavallazzi, Miramar, FL (US); Jose Luis Francese, Miami Springs, FL (US); Robert Sixto, Jr., Miami, FL (US)

(73) Assignee: Biomet C.V., Gibraltar (GI)

( * ) Notice: Subject to any disclaimer, the term of this patent is extended or adjusted under 35 U.S.C. 154(b) by 882 days.

(21) Appl. No.: 11/862,869

(22) Filed: Sep. 27, 2007

(65) Prior Publication Data

US 2009/0088807 A1    Apr. 2, 2009

(51) Int. Cl.
*A61B 17/80* (2006.01)
(52) U.S. Cl. ........................... 606/290; 606/298
(58) Field of Classification Search .............. 606/280, 606/286, 287, 290, 291, 298, 288, 71
See application file for complete search history.

(56) References Cited

U.S. PATENT DOCUMENTS

| | | | |
|---|---|---|---|
| 1,798,604 A | 3/1931 | Hoke | |
| 1,828,856 A | 10/1931 | Bridges | |
| 2,091,788 A | 8/1937 | McManus | |
| 2,965,205 A * | 12/1960 | Winchell | 192/66.23 |
| 3,596,656 A | 8/1971 | Kaute | |
| 3,741,205 A | 6/1973 | Markolf et al. | |
| 4,029,091 A | 6/1977 | Von Bezold et al. | |
| 4,794,918 A | 1/1989 | Wolter | |
| 5,057,111 A | 10/1991 | Park | |
| 5,151,103 A * | 9/1992 | Tepic et al. | 606/291 |
| 5,176,678 A | 1/1993 | Tsou | |
| 5,269,784 A | 12/1993 | Mast | |
| 5,275,601 A | 1/1994 | Gogolewski et al. | |
| 5,364,399 A | 11/1994 | Lowery et al. | |
| 5,520,690 A | 5/1996 | Errico et al. | |
| 5,531,746 A | 7/1996 | Errico et al. | |
| 5,549,608 A | 8/1996 | Errico et al. | |
| 5,554,157 A | 9/1996 | Errico et al. | |
| 5,584,834 A | 12/1996 | Errico et al. | |
| 5,586,984 A | 12/1996 | Errico et al. | |
| 5,601,553 A | 2/1997 | Trebing et al. | |
| 5,607,426 A | 3/1997 | Ralph et al. | |
| 5,607,428 A * | 3/1997 | Lin | 606/287 |

(Continued)

FOREIGN PATENT DOCUMENTS

DE    4341980    6/1995
DE    4343117    6/1995

(Continued)

*Primary Examiner* — Kevin T Truong
*Assistant Examiner* — Michael T Schaper
(74) *Attorney, Agent, or Firm* — Gordon & Jacobson, PC

(57) ABSTRACT

A polyaxial locking screw system includes a bone plate defining a plate hole with an inner spherical surface and a relatively harder split polyaxial bushing with a outer spherical surface provided within the plate hole for receiving a bone screw. In one embodiment, the plate is formed from titanium alloy, while the bushing is formed from a cobalt chrome alloy. The outer surface of the polyaxial bushing includes a plurality of spikes. When the screw is inserted into the bushing, since the bushing material is considerably harder than the plate material, the forceful expansion of the bushing during screw insertion causes the spikes to penetrate into the inner spherical surface of the hole, thereby increasing the frictional engagement of the bushing to the plate to lock the screw at a desired angle.

26 Claims, 3 Drawing Sheets

U.S. PATENT DOCUMENTS

| | | | |
|---|---|---|---|
| 5,643,265 A | 7/1997 | Errico et al. | |
| 5,647,873 A | 7/1997 | Errico et al. | |
| 5,709,686 A | 1/1998 | Talos et al. | |
| 5,735,853 A | 4/1998 | Olerud | |
| 5,797,912 A | 8/1998 | Runciman et al. | |
| 5,807,396 A | 9/1998 | Raveh | |
| 5,810,823 A | 9/1998 | Klaue et al. | |
| 5,954,722 A | 9/1999 | Bono | |
| 5,976,141 A | 11/1999 | Haag et al. | |
| 5,997,541 A | 12/1999 | Schenk | |
| 6,048,344 A | 4/2000 | Schenk | |
| 6,206,881 B1 | 3/2001 | Frigg et al. | |
| 6,235,033 B1 | 5/2001 | Brace et al. | |
| 6,280,445 B1 | 8/2001 | Morrison et al. | |
| 6,322,562 B1 | 11/2001 | Wolter | |
| 6,454,769 B2 | 9/2002 | Wagner et al. | |
| 6,485,491 B1* | 11/2002 | Farris et al. | 606/250 |
| 6,572,622 B1* | 6/2003 | Schafer et al. | 606/272 |
| 6,575,975 B2 | 6/2003 | Brace et al. | |
| 6,663,632 B1 | 12/2003 | Frigg | |
| 6,730,091 B1 | 5/2004 | Pfefferle et al. | |
| 6,755,831 B2* | 6/2004 | Putnam et al. | 606/311 |
| 6,955,677 B2 | 10/2005 | Dahners | |
| 6,974,461 B1 | 12/2005 | Wolter | |
| 7,276,070 B2* | 10/2007 | Muckter | 606/71 |
| 7,311,712 B2* | 12/2007 | Dalton | 606/71 |
| 7,682,379 B2* | 3/2010 | Mathieu et al. | 606/289 |
| 7,785,327 B1* | 8/2010 | Navarro et al. | 606/71 |
| 7,846,163 B2* | 12/2010 | Fourcault et al. | 606/68 |
| 8,216,283 B2* | 7/2012 | Mathieu et al. | 606/280 |
| 8,226,692 B2* | 7/2012 | Mathieu et al. | 606/280 |
| 8,287,575 B2* | 10/2012 | Murner et al. | 606/287 |
| 2002/0022843 A1 | 2/2002 | Michelson | |
| 2003/0083660 A1 | 5/2003 | Orbay | |
| 2003/0187440 A1* | 10/2003 | Richelsoph et al. | 606/61 |
| 2003/0199876 A1* | 10/2003 | Brace et al. | 606/69 |
| 2003/0225409 A1* | 12/2003 | Freid et al. | 606/69 |
| 2004/0073218 A1* | 4/2004 | Dahners | 606/69 |
| 2004/0092938 A1 | 5/2004 | Carli | |
| 2004/0127900 A1* | 7/2004 | Konieczynski et al. | 606/69 |
| 2004/0204712 A1* | 10/2004 | Kolb et al. | 606/69 |
| 2004/0220570 A1* | 11/2004 | Frigg | 606/69 |
| 2004/0254579 A1 | 12/2004 | Buhren et al. | |
| 2004/0260295 A1* | 12/2004 | Orbay et al. | 606/69 |
| 2004/0260298 A1* | 12/2004 | Kaiser et al. | 606/72 |
| 2004/0267261 A1* | 12/2004 | Derouet | 606/70 |
| 2005/0004574 A1 | 1/2005 | Muckter | |
| 2005/0033298 A1* | 2/2005 | Hawkes et al. | 606/61 |
| 2005/0043736 A1* | 2/2005 | Mathieu et al. | 606/73 |
| 2005/0049594 A1* | 3/2005 | Wack et al. | 606/69 |
| 2005/0154392 A1* | 7/2005 | Medoff et al. | 606/69 |
| 2005/0165400 A1* | 7/2005 | Fernandez | 606/69 |
| 2005/0182404 A1* | 8/2005 | Lauryssen et al. | 606/69 |
| 2005/0187551 A1* | 8/2005 | Orbay et al. | 606/69 |
| 2005/0192580 A1* | 9/2005 | Dalton | 606/73 |
| 2005/0228386 A1* | 10/2005 | Ziolo et al. | 606/69 |
| 2005/0240186 A1* | 10/2005 | Orbay | 606/69 |
| 2005/0251137 A1* | 11/2005 | Ball | 606/61 |
| 2005/0261690 A1* | 11/2005 | Binder et al. | 606/69 |
| 2005/0277937 A1* | 12/2005 | Leung et al. | 606/69 |
| 2006/0122602 A1* | 6/2006 | Konieczynski et al. | 606/69 |
| 2006/0149256 A1* | 7/2006 | Wagner et al. | 606/69 |
| 2006/0235399 A1 | 10/2006 | Carls | |
| 2007/0118125 A1* | 5/2007 | Orbay et al. | 606/69 |
| 2008/0172094 A1* | 7/2008 | Mathieu et al. | 606/280 |
| 2008/0221569 A1* | 9/2008 | Moore et al. | 606/53 |
| 2009/0192553 A1* | 7/2009 | Maguire et al. | 606/305 |
| 2010/0137867 A1* | 6/2010 | Mathieu et al. | 606/71 |
| 2010/0256686 A1* | 10/2010 | Fisher et al. | 606/286 |
| 2011/0196423 A1* | 8/2011 | Ziolo et al. | 606/246 |

FOREIGN PATENT DOCUMENTS

| | | |
|---|---|---|
| EP | 0486762 | 5/1992 |
| EP | 0530585 | 3/1993 |
| EP | 1364623 | 11/2003 |
| FR | 2667913 | 4/1992 |
| WO | WO 96/25892 | 8/1996 |
| WO | WO 96/32071 | 10/1996 |
| WO | WO 97/02786 | 1/1997 |
| WO | WO 97/09000 | 3/1997 |
| WO | WO 98/12976 | 4/1998 |
| WO | WO 01/03593 | 1/2001 |
| WO | WO 01/78615 | 10/2001 |
| WO | WO 02/45568 | 6/2002 |
| WO | WO 03/043513 | 5/2003 |
| WO | WO 03/055401 | 7/2003 |
| WO | WO 03/071965 | 9/2003 |
| WO | WO 03/101321 | 12/2003 |
| WO | WO 2004/032751 | 4/2004 |
| WO | WO 2004/043276 | 5/2004 |
| WO | WO 2004/052219 | 6/2004 |
| WO | WO 2004/066855 | 8/2004 |
| WO | WO 2004/069066 | 8/2004 |
| WO | WO 2004/096067 | 11/2004 |

* cited by examiner

LOCKING SCREW SYSTEM WITH RELATIVELY HARD SPIKED POLYAXIAL BUSHING

BACKGROUND OF THE INVENTION

1. Field of the Invention

This invention relates broadly to orthopedic plates. More particularly, this invention relates to plates that locks a fastener in a desired angular orientation relative to plate to maintain the desired angular orientation.

2. State of the Art

There has been a high level of interest by the orthopedic industry to develop locking fasteners for bone plates. The exact requirements vary for the locking fasteners used with each type of bone plate and the surgical indication. However, orthopedic surgeons generally prefer locking fasteners that are easy to insert and remove, reliably lock to the plate and are atraumatic to surrounding soft tissues. In addition, it is advantageous in certain situations to have a fastener that can be set in a surgeon-defined angle relative to the plate.

One such system meeting all the aforementioned requirements is the POLYAX locking screw system available from DePuy Spine, Inc., which is described in U.S. Pat. No. 5,954,722 to Bono et al. The POLYAX locking screw system allows the surgeon to angle the axis of the bone screw up to 15 degrees in any direction relative to the hole axis, and then to lock the screw head to the plate to maintain that angle. The POLYAX system includes a split bushing having an outer spherical shape that is assembled into a plate hole having a matching spherical contour. The bushing has a conical (6° included angle) threaded hole that receives a matching threaded head of the bone screw. A small pin pressed into a hole located on the perimeter of the plate hole aligns with the split of the bushing to prevent rotation of the bushing as the bone screw head engages the conical threaded hole of the bushing. Tightening of the bone screw expands the bushing against the inside surface of the plate hole and locks the screw to the plate. Both the POLYAX bushing and the bone plate are formed from a titanium alloy (Ti-6Al-4V) of similar hardness and smooth features.

The POLYAX locking plates can be used in various applications. By way of example, vertebral plates and periarticular plates can be assembled as POLYAX systems. With respect to a periarticular plate, bushings are currently provided in plates having a thickness of about 3 mm.

Proposed bone plates such as for elbow fractures have portions with a substantially smaller thickness of about 2 mm, one-third smaller in thickness. Portions of the bushing and screw head of the current POLYAX system, if assembled into a 2 mm thick bone plate and then angled to the maximum extent, would undesirably extend beyond the top and bottom surfaces of the bone plate. This may cause irritation of surrounding soft tissues or prevent the plate from seating properly against the bone. Simply reducing the overall height of the bushing would help to make the portions of the bushing and screw head less "proud" to the plate surfaces. However this also would reduce the area of the interfacing surfaces of the bushing and the plate hole, thereby reducing the frictional engagement and the overall locking force.

SUMMARY OF THE INVENTION

A polyaxial locking screw system for internal fixation of fractured bones according to the invention includes a bone plate defining a plate hole and a spiked relatively harder polyaxial bushing provided within the plate hole for receiving a bone screw.

The plate hole has a spherical inner surface, and preferably an antirotational feature formed on the inside spherical surface of the hole to prevent rotation of the bushing in the hole during insertion of the locking screw. The plate is preferably formed from a material having a hardness of 28-35 HRC, preferably titanium alloy.

The polyaxial bushing is a split ring split having a central threaded conical hole and an outer spherical surface. The outer surface includes a plurality of spikes. The polyaxial bushing is preferably formed from a material harder than that used to construct the bone plate, preferably having a hardness of 36-44 HRC, and most preferably CoCr alloy.

The screw includes a tapered threaded head that engages a conically hole in the bushing. The threads of the screw head and bushing may be configured such that a minor diametral surface of the screw head engages the bushing threads. This creates a substantial radial force on the bushing to aid in the frictional engagement of the bushing to the plate hole, thereby locking the screw at a desired articulation angle with respect to the axis of the plate hole. The hole of the bushing and head of the screw are designed to minimize vertical variability of where the screw head seats within the bushing. Since the bushing material is considerably harder than the plate material, the forceful expansion of the bushing during screw insertion causes the spikes to penetrate into the inner spherical surface of the hole, thereby further increasing the frictional engagement of the bushing to the plate to lock the screw at the desired angle.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
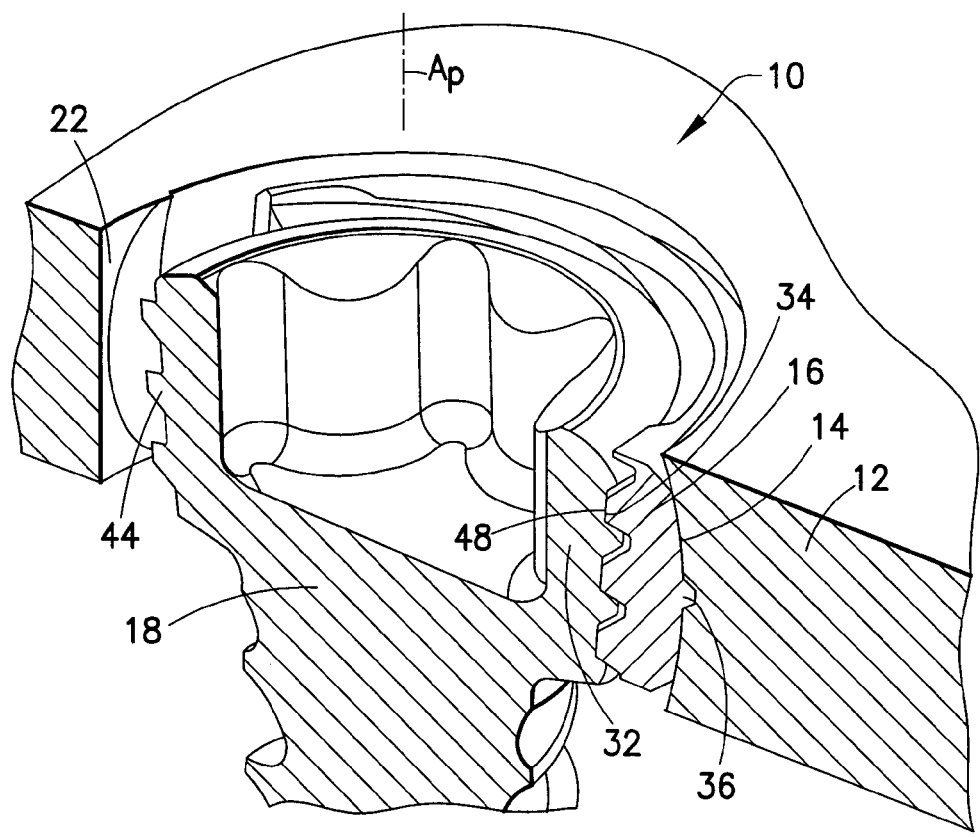
FIG. 1 a cross-sectional view of a polyaxial locking screw system according to the invention, with the screw fully inserted into the bushing and locked inside the plate hole in a centered position.

Turning now to FIG. 1, a locking screw system 10 for internal fixation of fractured bones according to the invention is shown. The locking screw system 10 includes a bone plate 12 defining a plate hole 14, a polyaxial bushing 16 provided within the plate hole 14, and a locking screw 18 (FIG. 2) receivable within bushing 16.

Figure 3:
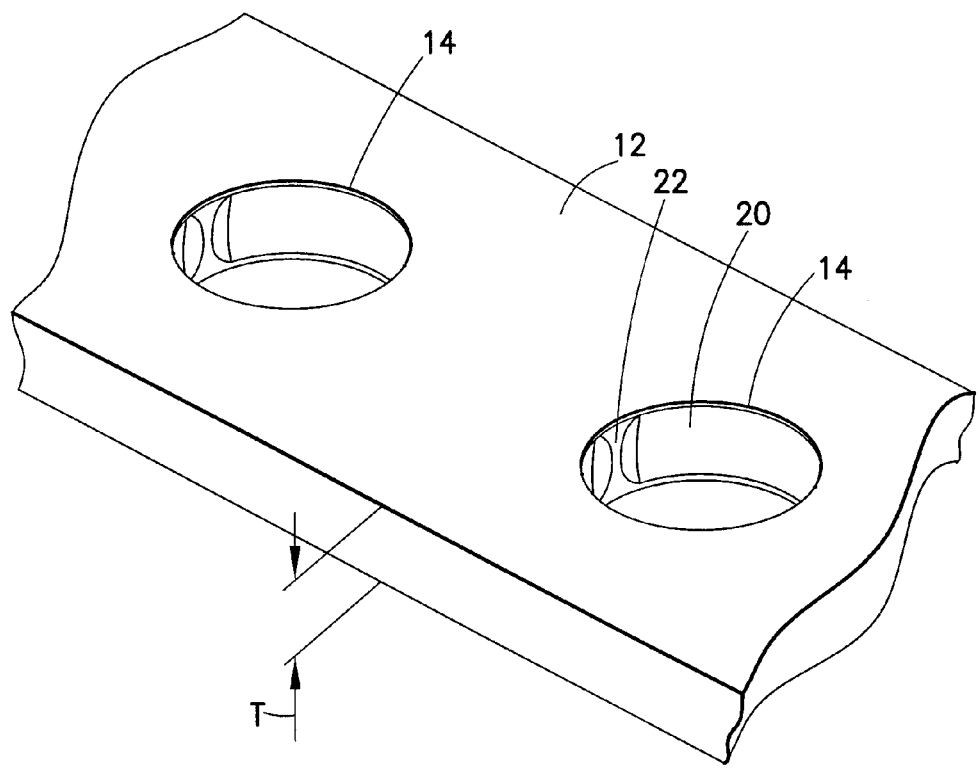
FIG. 3 is a perspective view of a portion of the bone plate of FIG. 1.

Referring to FIGS. 1 and 3, the plate 12 may include a plurality of plate holes 14. The plate hole 14 has a spherical inner wall surface 20 in which the bushing 16 is polyaxially articulatable. The plate hole 14 preferably has an antirotational feature 22 formed on the inner spherical surface 20 of the plate hole to limit or control freedom of movement of the bushing 16 in the hole relative to axis A during insertion of the locking screw 18 (which would otherwise inhibit insertion of locking screw therein). The antirotational feature 22 can be sized and oriented in any position around the circumference of surface 20 such that the optimal freedom of movement or lack their of is achieved. That is, if the predicted direction of desired screw angulation is known or a direction that is not desirable is known (e.g., where there is a potential for a screw to enter an articulating surface, exiting the bone, or entering an unintended bone, or for two or more screws interfering with one another), then the size and location of the feature can be modified to achieve the desired degree of freedom. Such modification is described in more detail below. The antirotational feature 22 replaces a pin used in the current POLYAX system. As the plate 12 is thinner (thickness T) than plates used with the prior POLYAX system (e.g., T is preferably less than 3 mm and approximately 2 mm in thickness), forming the antirotational feature 22 integrally with the plate is preferred in comparison to assembling a shorter pin into the plate. Moreover, by integrating the antirotational feature within the plate, the number of discrete components required for the system is reduced relative to the prior system. The plate 12 is preferably formed from a biocompatible metal, for example, a titanium alloy (TI-6Al-4V) having a hardness of 28-35 HRC.

Figure 4:
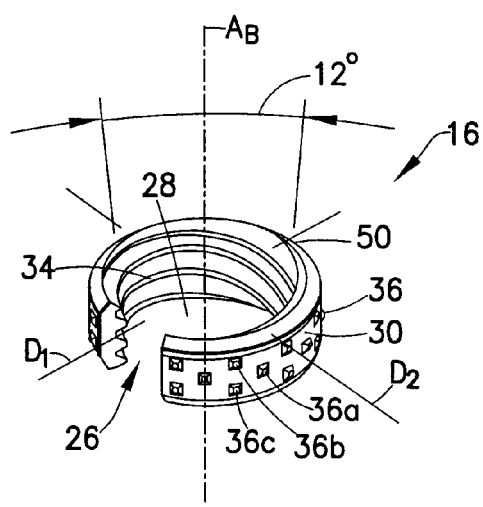
FIG. 4 is a perspective view of a bushing of the polyaxial locking screw system of FIG. 1.

Referring to FIG. 4, the polyaxial bushing 16 is a split ring split at 26. If the bushing 16 is compressed in diameter for insertion into the plate hole 14, the bushing must remain in the elastic region when compressed for installation within the plate hole 14; i.e., it must not plastically deform. This can be achieved with a spring-like feature in one section of the bushing (e.g., opposite split 26) or a simple reduction in cross section along a portion of the bushing. Alternatively, as discussed below, the bushing can be installed without compressing it.

The bushing 16 has a central radially interior conical hole 28 and a radially exterior outer surface 30. The conical hole 28 preferably has an included angle of substantially 12° (i.e., 12°±2°) (compared to the included angle of 6° on the conical hole of the POLYAX bushing). This actually reduces mechanical advantage relative to the POLYAX system, but provides the advantage of reduced vertical variability of where the head 32 of the locking screw 18 seats within the conical hole 28 of the bushing 16 (FIG. 1). The vertical potential variability is approximately inversely proportional to the taper angle, at 10 to 1 for a 6° included angled (i.e., the prior POLYAX system) and 5 to 1 for a 12° included angled. Vertical variability is particularly important for a thin plate, e.g., a 2 mm plate, where structural integrity is compromised with uncontrolled or too much vertical variability. The conical hole 28 is preferably threaded with a triple lead thread 34.

Referring to FIG. 4, the outer surface 30 of the bushing 16 is preferably spherically contoured and dimensioned so that it can fit in and articulate within the plate hole. Alternatively, the outer surface 30 can be other shapes that articulate within in a spherical contour. For example, the outer surface of the bushing could be shaped as a series of steps or facets, or a combination of steps and facets. The outer surface 30 is provided with a plurality of spikes 36. In the embodiment shown in FIG. 4, the bushing has thirty-two (32) spikes 36, but the number of spikes may vary between, by way of example (and not limitation), eight (8) and over thirty-two (32) spikes.

The spikes 36 may be spaced apart or be grouped or uniformly arranged around the outer surface 30. It is preferable that the spikes be both evenly spaced in a both an equatorial and polar configuration. That is, the spikes are preferably evenly distributed radially about the circumference as well as in at least three layers. A center or middle layer 36a is aligned over a plane extending perpendicular to the axis $A_B$ of the bushing and halfway thru the length of the bushing, and second and third layers 36b, 36c are provided above and below the center layer 36a, respectively, such that when the bushing 16 is tilted 15° off of the axis $A_P$ of the plate hole 14, all spikes 36 (or a substantial majority) are still contained within the spherical hole, yet are as far as possible from the center layer to increase stability within the plate.

Figure 5:
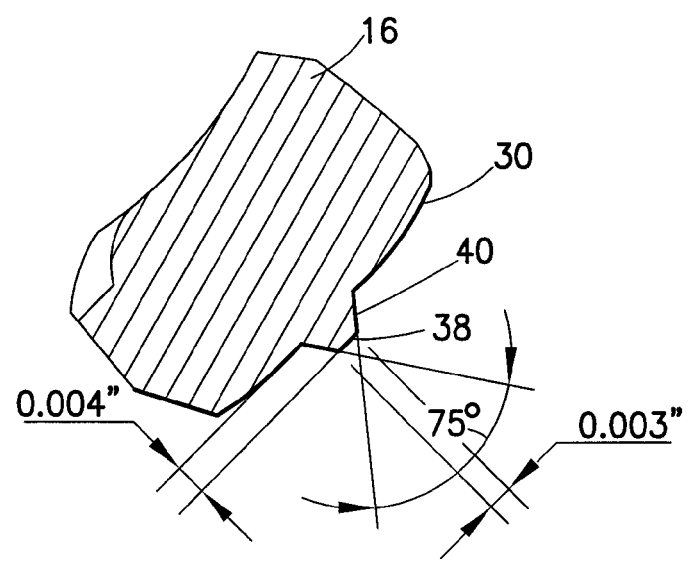
FIG. 5 is a cross-sectional, detailed view of the bushing shown in FIG. 4.

Referring to FIG. 5, the spikes 36 are preferably of a frusto-pyramidal shape. As shown in FIG. 5, one embodiment of a spike 36 stands proud of the outer surface 30 by approximately 0.004 inch, has a tip diameter, i.e., a cross-dimension, at truncation 38 of approximately 0.003 inch, and has sides 40 angled at an included angle of 75°. Other shapes, including conical and frustoconical, and other dimensions are possible.

The polyaxial bushing 16 is preferably formed from a material harder than that used to construct the bone plate 12, such as cobalt chrome (CoCr) alloy, and preferably has a hardness of 36-44 HRC. The CoCr alloy, besides having a desired hardness and ability to penetrate the titanium alloy of the plate, provides for a more lubricious interface with the screw 18, described below, and plate 12 since it is a different material than each. In addition, the CoCr alloy does not gall as easily as the titanium alloy.

Figure 2:
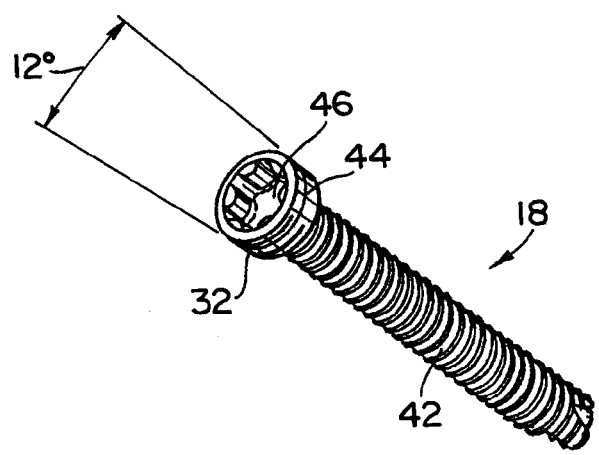
FIG. 2 is a perspective view of a locking bone screw for use in the polyaxial screw system of FIG. 1.

Referring to FIGS. 1 and 2, the screw 18 includes a threaded shaft 42 that extends through the bushing 16 and into bone, and a tapered threaded head 32 that engages the conical hole 28 in the bushing 16. The included angle of the taper of the screw head 32 is substantially 12° (i.e., 12°±2°) (in comparison to the 6° included angle of the POLYAX screw head) and corresponds to the included angle of the conical hole 28 in the bushing. The threads 44 about the head 32 are tapered, triple lead threads that matches the thread 34 on the head of the locking screw, and is generally shorter in height and number of threads than on the head of the prior POLYAX screw. The screw head 32 preferably includes a hexalobe socket 46 to maximize torque transmission within a shallow design.

Referring particularly to FIG. 1, the threads 34, 44 of the bushing 16 and screw head 32 may be configured such that a minor diametral surface 48 of the screw head 18 engages the bushing threads 34. This thread configuration causes a larger portion of the screw insertion force to be directed in the radial direction (for expanding the bushing) rather than in the axial direction (for advancing the screw) as compared to conventional screw thread systems. As such, a substantial radial force is provided to the bushing 16 to aid in the frictional engagement of the bushing 16 to the plate 12 at the plate hole 14, thereby locking the screw 18 at a desired angle with respect to the axis $A_P$ of the plate hole. The increased force of this design mitigates the loss in mechanical advantage by the larger taper angle of the screw head and conical hole of the bushing.

Since the material of the bushing 16 is considerably harder than the material of the plate 12, the forceful expansion of the bushing 16 during insertion of the screw 18 causes the spikes 36 to penetrate into the inner spherical surface 20 of the plate hole 14, thereby further increasing the frictional engagement of the bushing 16 to the plate 12 to lock the screw at the desired angle. The number and size of the spikes 36 are designed to achieve about 0.002 inch depth of penetration into the surface 20 of the plate hole. The optimal number of spikes 36 and their shape is determined by the contact area between the spikes 36 on the outer surface 30 of the bushing 16 and the spherical wall surface 20 of the plate hole 14 on the plate 12, and the capacity of the screw 18 to exert an expansion force onto the bushing 16, such that the spikes 36 will deform (dig into) the wall surface 20 of the plate. If the cross-sectional area of interference (between spikes and plate) is too large, the spikes will not displace plate material around them. If the cross-sectional interference is too small, the system will not withstand the desired bending loads to the screw.

In the preferred embodiment, the maximum angle that may be achieved is approximately 15° in any direction with respect to the hole axis for a size 4.00 mm screw. The maximum angle is greater than 15° for smaller screws. However, the angle in any direction can be limited or controlled. The antirotational feature 22 is preferably provided at a location on the hole that limits movement of the bushing in a non-desired orientation (i.e., where otherwise a screw inserted through the bushing could extend through a bone articulation surface, could extend outside the bone on which the plate is implanted, or could interfere with another bone, or where two or more screws could potentially interfere with each other). It is also appreciated that the bushing 16 and antirotational feature 22 can be structured to allow greater relative movement. For example, the bushing may be split such that the material of the bushing extends about more than 181° but less, 320±30°. In such range, the bushing has a large freedom of articulation relative to the bushing, but will be prevented from rotation within a maximum of 180° of rotation relative to the plate hole. Increased freedom of movement in all directions is provided at the expense of reduced gripping strength.

Several tests were conducted to compare the locking force of the present screw locking system to the prior POLYAX screw system. In one test, the results of which are shown in Table 1, the locking force of a 3.5 mm POLYAX bone screw inserted into Ti-6Al-4V alloy bushing provided in a 2 mm Ti-6Al-4V alloy test plate was compared to the locking force of 3.5 mm bone screws inserted into spiked CoCr alloy bushings provided in a 2 mm Ti-6Al-4V alloy test plates according to the invention. The locking force (or force to bend or move the respective screws inserted into the plate at a particular insertion torque) was measured by determining what force (bending moment) applied perpendicularly to the end of the screws at a distance of 25.4 mm from the bottom of the test plate caused the screws to move relative to the plate.

inserted with 20 in-lbs was found to be 20.1 in-lbs; and the average locking force for the locking screw system of the invention with thirty-two (32) spikes and inserted with 25 in-lbs was found to be 20.9 in-lbs.

Referring to FIGS. 3 and 4, a preferred method of installing the bushing 16 into the plate hole 14 is now described. The diameter of the bushing 16 from surface spike to surface spike is generally sufficiently large to prevent the bushing from releasing from the plate hole 14. However, the diameter $D_1$ of the bushing from the split 26 to the opposite side 50 of the bushing is appropriately sized such that the bushing may be inserted orthogonally to the plate hole and into the hole. It may be necessary to remove one or more spikes lying substantially along $D_1$ and near opposite side 50 (i.e., within 5°) to reduce the effective bushing diameter and facilitate insertion. Once inserted into the plate hole, the bushing is orientated to align the split 26 with the antirotational feature 22 of the plate hole 14. In another embodiment, preferably two spikes (although possibly more spikes) lying substantially along a diameter $D_2$ (i.e., within 5°) orientated orthogonal to a diameter $D_1$ are removed to reduce diameter $D_2$, and the bushing is inserted with such reduced diameter $D_2$ so as to be received within the plate hole 14. Once inserted into the plate hole 14, the bushing 16 is orientated to align the split 26 with the antirotational feature 22. The bushing 16 can alternatively be elastically compressed and inserted into the plate hole 14.

There have been described and illustrated herein embodiments of a screw locking system. While particular embodiments of the invention have been described, it is not intended that the invention be limited thereto, as it is intended that the invention be as broad in scope as the art will allow and that the specification be read likewise. Thus, while particular materials have been disclosed, it will be appreciated that other materials can be used as well. In addition, while particular shapes of spikes, and numbers thereof, have been disclosed, it will be understood other shapes and numbers of spikes or other protuberances (collectively referred to herein as 'spikes') can be used. It will therefore be appreciated by those skilled in the art that yet other modifications could be made to the provided invention without deviating from its spirit and scope as claimed.

TABLE 1

Measured Locking Force of Screw Relative to Plate

| Locking System | # of Spikes | Screw Diam. (mm) | Input Torque (in-lbs) | Bending Moment Test 1 (in-lbs) | Bending Moment Test 2 (in-lbs) | Bending Moment Test 3 (in-lbs) | Bending Moment Test 4 (in-lbs) | Avg. Bending Moment (in-lbs) |
|---|---|---|---|---|---|---|---|---|
| Ti alloy plate/ Ti alloy bushing | 0 | 3.5 | 20 | | | | | 14.15 |
| Ti alloy plate/ CoCr bushing | 24 | 3.5 | 20 | 17.1 | 14.9 | 17.2 | 16.2 | 16.4 |
| Ti alloy plate/ CoCr bushing | 24 | 3.5 | 25 | 16 | 18.8 | 19.3 | 20.9 | 18.8 |
| Ti alloy plate/ CoCr bushing | 32 | 3.5 | 20 | 19.7 | 19.6 | 19.7 | 21.4 | 20.1 |
| Ti alloy plate/ CoCr bushing | 32 | 3.5 | 25 | 22 | 19.7 | 19.3 | 22.5 | 20.9 |

The average locking force for the prior POLYAX system inserted with 20 in-lbs of torque was found to be 14.15 in-lbs, whereas the average locking force for the locking screw system of the invention with twenty-four (24) spikes and inserted with 20 in-lbs was found to be 16.4 in-lbs; the average locking force for the locking screw system of the invention with twenty-four (24) spikes and inserted with 25 in-lbs was found to be 18.8 in-lbs; the average locking force for the locking screw system of the invention with thirty-two (32) spikes and

What is claimed is:

1. A locking plate system for engagement with a bone, the system comprising:
   a) a plate including a plate hole with an inner wall;
   b) a split bushing including a radially exterior surface and a radially interior hole, said exterior surface including a plurality of frusto-pyramidal spikes, each of said spikes having four sides of substantially common shape and size, each of said four sides of a spike extends up from said exterior surface of said bushing by approximately 0.004 inch, said four sides are angled at an included angle of 75°, and a cross-dimension of a frustum of a tip of said spike is approximately 0.003 inch, and multiple spikes are provided about a line defining a circumference, said exterior surface of said bushing is sized to be in contact with said inner wall and said bushing is polyaxially articulatable within said plate hole; and c) a bone screw including a leading portion sized for extension through said hole in said bushing and into the bone and an opposite head portion sized to expand said bushing against the inner wall of said plate to cause said spikes to penetrate said inner wall and lock said bushing and said plate in a selected polyaxial position.

2. A locking plate system according to claim 1, wherein:
said plate hole is provided with an antirotational feature formed on said inner wall to prevent rotation of said bushing in the plate hole about the central axis during insertion of said locking screw, said antirotational feature includes a groove extending only partially circumferentially about said inner wall, said groove sized to receive an entirety of said exterior surface of said bushing.

3. A locking plate system according to claim 1, wherein:
said plate is less than 3 mm in thickness.

4. A locking plate system according to claim 1, wherein:
said exterior surface of said bushing has a circumference defining a plane perpendicular to a central axis through said bushing,
said plurality of spikes are evenly radially distributed about said circumference, and
all of said plurality of spikes being divided into one of first, second and third subsets about said circumference, each of said subsets having a substantially equal number of at least two of said spikes,
said first subset is distributed in said plane perpendicular,
said second subset is distributed above said plane perpendicular, and
said third subset is distributed below said plane perpendicular.

5. A locking plate system according to claim 1, wherein:
said radial interior hole of said bushing and said head portion of said screw each having an included angle of substantially 12°.

6. A locking plate system according to claim 1, wherein:
said plate is 2 mm thick and includes a bone contacting surface, and when said locking screw is inserted into said bushing with a torque of 20 in-lbs to expand said bushing and lock said locking screw relative to said plate, a force in excess of 16 lbs applied perpendicularly to said locking screw at a distance of 25.4 mm from said bone contacting surface of said plate is required to move said locking screw relative to said plate.

7. A locking plate system according to claim 1, wherein:
said spikes each have a substantially square base.

8. A locking plate system according to claim 1, wherein:
said plate is 2 mm thick and includes a bone contacting surface, and once said locking screw has been inserted into said bushing with a torque of 20 in-lbs such that said bushing is expanded and said locking screw is locked relative to said plate, a force in excess of 16 lbs applied perpendicularly to said locking screw at a distance of 25.4 mm from said bone contacting surface of said plate is required to move said locking screw relative to said plate.

9. A locking plate system according to claim 1, wherein:
said bushing includes split ends about which said bushing is expandable, and
said plate hole is provided with an antirotational feature formed on said inner wall to prevent rotation of said bushing in the plate hole about the central axis during insertion of said locking screw, said antirotational feature includes a structure that extends from said inner wall to between said split ends.

10. A locking plate system for engagement with a bone, the system comprising:
a) a plate including a plate hole with an inner wall and a central longitudinal axis extending through said plate hole, said plate made of a first material having a first hardness;
b) a split bushing including a radially exterior surface and a radially interior hole and defining a central axis, said exterior surface including a plurality of spikes radially and longitudinally offset from each other, a plurality of said spikes being distributed within each of at least three planes, one of said planes being a middle plane between the other two planes, each of said planes being axially displaced along and perpendicular to said central axis of said bushing, said bushing polyaxially articulatable within said plate hole, and said bushing made of a second material having a second hardness; and
c) a bone screw including a leading portion sized for extension through said hole in said bushing and into the bone and an opposite head portion sized to expand said bushing against the inner wall of said plate to locking said bushing and said plate in a selected polyaxial position, wherein said second hardness is sufficiently greater than said first hardness such that said spikes penetrate said inner surface of said plate hole upon expansion of said bushing,
said plate hole is provided with an antirotational feature formed on said inner wall to prevent rotation of said bushing in said plate hole about said central longitudinal axis during insertion of said bone screw, said antirotational feature includes a groove extending only partially circumferentially about said inner wall, said groove sized to receive an entirety of said exterior surface of said bushing, and
said bushing includes split ends about which said bushing is expandable, and said antirotational feature includes a structure that extends from said inner wall to between said split ends.

11. A locking plate system according to claim 10, wherein:
said plate is less than 3 mm in thickness.

12. A locking plate system according to claim 10, wherein:
said spikes are frusto-pyramidal in shape, and have four sides of substantially common shape and size.

13. A locking plate system according to claim 10, wherein:
said plurality of spikes are evenly radially distributed about said circumference, and
all of said plurality of spikes being divided into one of first, second and third subsets about said circumference, each of said subsets having a substantially equal number of at least two of said spikes,
said first subset is distributed in said middle plane,
said second subset is distributed above said middle plane, and
said third subset is distributed below said middle plane.

14. A locking plate system according to claim 10, wherein:
said radial interior hole of said bushing and said head portion of said screw each having an included angle of substantially 12°.

15. A locking plate system for engagement with a bone, the system comprising:
  a) a plate including a plate hole with an inner wall and a central longitudinal axis extending through said plate hole, said plate made of a first material having a hardness of 28-35 HRC;
  b) a split bushing including a radially exterior surface and a radially interior hole and defining a central axis, said exterior surface including a plurality of frusto-pyramidal spikes with a substantially square shaped base, said spikes radially and longitudinally offset from each other, a plurality of said spikes being distributed within each of at least three planes, one of said planes being a middle plane between the other two planes, said planes being axially displaced along and perpendicular to said central axis of said bushing, said bushing polyaxially articulatable within said plate hole, and said bushing made of a material having a hardness of 36-44 HRC; and
  c) a bone screw including a leading portion sized for extension through said hole in said bushing and into the bone and an opposite head portion sized to expand said bushing against the inner wall of said plate to cause said spikes to penetrate said inner wall and thereby lock said bushing and said plate in a selected polyaxial position,
    said plate hole is provided with an antirotational feature formed on said inner wall to prevent rotation of said bushing in said plate hole about said central longitudinal axis during insertion of said bone screw, said antirotational feature includes a groove extending only partially circumferentially about said inner wall, said groove sized to receive an entirety of said exterior surface of said bushing, and
    said bushing includes split ends about which said bushing is expandable, and said antirotational feature includes a structure that extends from said inner wall to between said split ends.

16. A locking plate system according to claim 15, wherein: said plate is less than 3 mm in thickness.

17. A locking plate system according to claim 15, wherein: said spikes each have four sides of substantially common shape and size.

18. A locking plate system according to claim 15, wherein: said bushing is insertable into said plate hole without using compression.

19. A locking plate system according to claim 15, wherein: said radial interior hole of said bushing and said head portion of said screw each having an included angle of substantially 12°.

20. A locking plate system for engagement with a bone, the system comprising:
  a) a plate including a plate hole with an inner wall and a central longitudinal axis extending through said plate hole, said plate made of a titanium alloy;
  b) a split bushing including a radially exterior surface and a radially interior conical hole and defining a central axis, said exterior surface including a plurality of spikes radially and longitudinally offset from each other, a plurality of said spikes being distributed within each of at least three planes, one of said planes being a middle plane between the other two planes, said planes being axially displaced along and perpendicular to said central axis of said bushing, said bushing polyaxially articulatable within said plate hole, and said bushing made of a cobalt chrome alloy; and
  c) a locking screw including a leading portion sized for extension through said conical hole in said bushing and into the bone and an opposite threaded head portion sized to expand said bushing against said inner wall of said plate hole to cause said cobalt chrome alloy spikes to penetrate said titanium alloy inner wall and thereby lock said bushing and said locking screw relative to said plate in a selected polyaxial position,
    said plate hole is provided with an antirotational feature formed on said inner wall to prevent rotation of said bushing in said plate hole about said central longitudinal axis during insertion of said locking screw, said antirotational feature includes a groove extending only partially circumferentially about said inner wall, said groove sized to receive an entirety of said exterior surface of said bushing, and
    said bushing includes split ends about which said bushing is expandable, and said antirotational feature includes a structure that extends from said inner wall to between said split ends.

21. A locking plate system according to claim 20, wherein: said plate is less than 3 mm in thickness.

22. A locking plate system according to claim 20, wherein: said spikes are frusto-pyramidal in shape, and have four sides of substantially common shape and size.

23. A locking plate system according to claim 22, wherein: each of said four sides extends up from said outer surface of said bushing by approximately 0.004 inch and is angled at an included angle of 75°.

24. A locking plate system according to claim 23, wherein: a cross-dimension of a frustum of a tip of at least one of said spikes is approximately 0.003 inch.

25. A locking plate system according to claim 20, wherein: said plurality of spikes are evenly radially distributed about said exterior surface, and
  said plurality of spikes being divided into one of first, second and third subsets about said exterior surface, each of said subsets having a substantially equal number of at least two of said spikes,
  said first subset is distributed in said middle plane,
  said second subset is distributed above said middle plane, and
  said third subset is distributed below said middle plane.

26. A locking plate system according to claim 20, wherein: said radial interior hole of said bushing and said head portion of said screw each have an included angle of substantially 12°.

* * * * *